United States Patent
Howard et al.

(10) Patent No.: US 12,408,919 B2
(45) Date of Patent: Sep. 9, 2025

(54) CATHETER WITH RADIOFREQUENCY CUTTING TIP AND HEATED BALLOON

(71) Applicant: Boston Scientific Scimed, Inc., Maple Grove, MN (US)

(72) Inventors: John F. Howard, Salem, MA (US); Gerald Fredrickson, Westford, MA (US); Kristin Regan, Winchester, MA (US); Gary A. Jordan, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 222 days.

(21) Appl. No.: 17/229,673

(22) Filed: Apr. 13, 2021

(65) Prior Publication Data

US 2021/0228210 A1    Jul. 29, 2021

Related U.S. Application Data

(63) Continuation of application No. 15/899,985, filed on Feb. 20, 2018, now Pat. No. 11,000,283, which is a
(Continued)

(51) Int. Cl.
*A61B 18/14* (2006.01)
*A61B 17/11* (2006.01)
(Continued)

(52) U.S. Cl.
CPC .. *A61B 17/1114* (2013.01); *A61B 17/320016* (2013.01); *A61B 18/1492* (2013.01);
(Continued)

(58) Field of Classification Search
CPC ........ A61B 17/1114; A61B 17/320016; A61B 18/1492; A61B 2017/00278;
(Continued)

(56) References Cited

U.S. PATENT DOCUMENTS

| 4,754,752 A | 7/1988 | Ginsburg et al. |
| 4,990,139 A | 2/1991 | Jang |

(Continued)

FOREIGN PATENT DOCUMENTS

| CN | 102379762 A | 3/2012 |
| EP | 0778010 A2 | 6/1997 |

(Continued)

OTHER PUBLICATIONS

Extended European Search Report 18165180.3 dated (Oct. 22, 2018) for Application Number (7 pages).
(Continued)

*Primary Examiner* — Michael F Peffley
(74) *Attorney, Agent, or Firm* — Seager, Tufte & Wickhem, LLP

(57) ABSTRACT

Methods for draining pseudocysts and stent delivery systems for use therein are disclosed. An illustrative system may include a catheter shaft having an inflatable balloon affixed to a distal end region thereof. A cutting electrode may be disposed at the distal end of the system and at least one heating electrode may be disposed within the inflatable balloon. A self expandable stent may be disposed about the inflatable balloon. The stent may be formed of a shape memory polymer. The inflation fluid may be heated within the balloon to facilitate expansion of the stent.

20 Claims, 15 Drawing Sheets

Related U.S. Application Data continuation of application No. 14/724,480, filed on May 28, 2015, now Pat. No. 9,913,649.

(60) Provisional application No. 62/004,003, filed on May 28, 2014.

(51) Int. Cl.
| | | |
|---|---|---|
| *A61B 17/32* | (2006.01) | |
| *A61F 2/04* | (2013.01) | |
| *A61F 2/958* | (2013.01) | |
| *A61B 17/00* | (2006.01) | |
| *A61B 18/00* | (2006.01) | |

(52) U.S. Cl.
CPC ............... *A61F 2/04* (2013.01); *A61F 2/958* (2013.01); *A61B 2017/00278* (2013.01); *A61B 2017/00818* (2013.01); *A61B 2017/00867* (2013.01); *A61B 2017/1139* (2013.01); *A61B 2018/0022* (2013.01); *A61B 2018/00494* (2013.01); *A61B 2018/00601* (2013.01); *A61F 2002/045* (2013.01); *A61F 2002/9583* (2013.01); *A61F 2210/0033* (2013.01); *A61F 2230/0069* (2013.01); *A61F 2230/0078* (2013.01); *A61F 2250/0003* (2013.01); *A61F 2250/0039* (2013.01)

(58) Field of Classification Search
CPC ........... A61B 2017/00818; A61B 2017/00867; A61B 2017/1139; A61B 2018/0022; A61B 2018/00494; A61B 2018/00601; A61F 2/04; A61F 2/958; A61F 2002/045; A61F 2002/9583; A61F 2210/0033; A61F 2230/0069; A61F 2230/0078; A61F 2250/0003; A61F 2250/0039
See application file for complete search history.

(56) References Cited

U.S. PATENT DOCUMENTS

| | | | |
|---|---|---|---|
| 4,998,933 A * | 3/1991 | Eggers | A61B 18/1492 606/41 |
| 5,178,620 A * | 1/1993 | Eggers | A61B 18/1492 606/41 |
| 5,292,321 A * | 3/1994 | Lee | A61B 17/22 606/198 |
| 5,843,116 A | 12/1998 | Crocker et al. | |
| 5,860,951 A | 1/1999 | Eggers et al. | |
| 5,944,738 A | 8/1999 | Amplatz et al. | |
| 6,022,359 A | 2/2000 | Frantzen | |
| 6,053,913 A | 4/2000 | Tu et al. | |
| 6,113,609 A | 9/2000 | Adams | |
| 6,290,485 B1 | 9/2001 | Wang | |
| 6,447,533 B1 | 9/2002 | Adams | |
| 6,488,653 B1 | 12/2002 | Lombardo | |
| 6,562,031 B2 * | 5/2003 | Chandrasekaran | A61M 25/10 606/41 |
| 6,620,122 B2 | 9/2003 | Stinson et al. | |
| 6,830,575 B2 | 12/2004 | Stenzel et al. | |
| 6,835,189 B2 | 12/2004 | Musbach et al. | |
| 7,200,445 B1 | 4/2007 | Dalbec et al. | |
| 8,133,199 B2 | 3/2012 | Weber et al. | |
| 8,357,193 B2 | 1/2013 | Phan et al. | |
| 8,454,632 B2 | 6/2013 | Binmoeller et al. | |
| 8,460,357 B2 | 6/2013 | McGarry et al. | |
| 8,617,196 B2 | 12/2013 | Binmoeller | |
| 9,668,853 B2 | 6/2017 | Shin | |
| 2001/0029352 A1 | 10/2001 | Gandhi et al. | |
| 2002/0161341 A1 | 10/2002 | Stinson et al. | |
| 2003/0040803 A1 | 2/2003 | Rioux et al. | |
| 2004/0167600 A1 | 8/2004 | LaFont et al. | |
| 2005/0010275 A1 | 1/2005 | Sahatjian et al. | |
| 2005/0056292 A1 | 3/2005 | Cooper | |
| 2005/0216074 A1 | 9/2005 | Sahatjian et al. | |
| 2006/0111704 A1 | 5/2006 | Brenneman et al. | |
| 2006/0211984 A1 | 9/2006 | Blank et al. | |
| 2006/0217748 A1 | 9/2006 | Ortiz | |
| 2007/0135825 A1 | 6/2007 | Binmoeller | |
| 2009/0143713 A1 * | 6/2009 | Van Dam | A61M 27/008 604/9 |
| 2009/0182412 A1 * | 7/2009 | Tan | A61F 2/966 604/509 |
| 2009/0281379 A1 | 11/2009 | Binmoeller et al. | |
| 2010/0268029 A1 * | 10/2010 | Phan | A61M 25/09 600/115 |
| 2011/0054381 A1 | 3/2011 | Van Dam et al. | |
| 2011/0190662 A1 | 8/2011 | McWeeney | |
| 2011/0307070 A1 | 12/2011 | Clerc et al. | |
| 2012/0283814 A1 | 11/2012 | Huang et al. | |
| 2013/0066315 A1 | 3/2013 | Subramaniam et al. | |

FOREIGN PATENT DOCUMENTS

| | | |
|---|---|---|
| EP | 1132059 A1 | 9/2001 |
| EP | 0778010 B1 | 9/2003 |
| EP | 1501448 B1 | 12/2008 |
| JP | H11502144 A | 2/1999 |
| WO | 9315787 A1 | 8/1993 |
| WO | 9718768 A1 | 5/1997 |
| WO | 9840033 A2 | 9/1998 |
| WO | 2004032799 A2 | 4/2004 |
| WO | 2004110313 A1 | 12/2004 |
| WO | 2012071388 A2 | 5/2012 |
| WO | 2012122157 A1 | 9/2012 |

OTHER PUBLICATIONS

Binmoeller et al; "A Novel Lumen-Apposing Stent for Transluminal Drainage of Nonadherent Extraintestinal Fluid Collections", Endoscopy vol. 43, Issue 4, pp. 337-342. 2011.

Binmoeller et al; "Endoscopic Ultrasound Guided Gastroenterostomy using Novel Tools Designed for Transluminal Therapy: a Porcine Study." Endoscopy vol. 44, pp. 499-503, 2012.

Binmoeller et al; "A Kit for EUS-Guided Access and Drainage of Pancreatic Pseudocysts: Efficacy in a Porcine Model," Spring Publishing, vol. 1, Issue 3, 2012.

* cited by examiner

CATHETER WITH RADIOFREQUENCY CUTTING TIP AND HEATED BALLOON

CROSS-REFERENCE TO RELATED APPLICATIONS

This application is a continuation of and claims the benefit of priority to U.S. patent application Ser. No. 15/899,985, filed on Feb. 20, 2018, now granted as U.S. Pat. No. 11,000,283 and claims the benefit of priority to, U.S. patent application Ser. No. 14/724,480, filed May 28, 2015, now granted as U.S. Pat. No. 9,913,649, which claims the benefit of priority under 35 U.S.C. § 119 to U.S. Provisional Application Ser. No. 62/004,003, filed May 28, 2014, the entire disclosures of which are herein incorporated by reference in their entirety.

TECHNICAL FIELD

The present disclosure relates generally to gastric pseudocyst drainage and relates more particularly to a method for draining gastric pseudocysts and to a stent delivery system for use in said method.

BACKGROUND

A gastric or pancreatic pseudocyst is a localized fluid collection, which may be rich in pancreatic enzymes, surrounded by a thin wall that may develop in the peritoneal cavity after the onset of acute pancreatitis. Although many pseudocysts resolve themselves spontaneously, some pseudocysts become quite large and require treatment due to the unwanted pressure they exert against the stomach and/or neighboring organs.

One approach to treating gastric pseudocysts involves surgery and typically comprises (i) cutting through the abdominal wall of the patient to permit access to the pseudocyst through the abdominal wall, (ii) perforating or puncturing the pseudocyst, (iii) inserting a drainage tube into the pseudocyst through the perforation to allow the contents of the pseudocyst to empty through the drainage tube to a point external to the patient, (iv) removing the drainage tube from the patient once the pseudocyst has been emptied, and (v) repairing the abdominal wall. As can readily be appreciated, the surgical approach described above is invasive and has easily identifiable drawbacks associated therewith, such as an appreciable risk of infection.

In some instances, an endoscopic approach to treating gastric pseudocysts may be utilized. This approach is less invasive than surgery and typically involves inserting an endoscope through the patient's mouth and into the patient's stomach. The endoscope is first used to visually locate the pseudocyst on the opposite side of the stomach wall. A needle or sphincterotome is then extended through the distal end of the endoscope to perforate both the stomach wall and the pseudocyst. A contrast agent delivered through the endoscope is then injected into the pseudocyst, and a cystogram is endoscopically performed to confirm entry into a pseudocyst (as opposed to entry into the peritoneal cavity). Following confirmation of entry into a pseudocyst, a guide wire is advanced through the endoscope and into the pseudocyst. Next, a balloon catheter is advanced through the endoscope and over the guide wire into the pseudocyst. The balloon is dilated to enlarge the perforations in the pseudocyst and the stomach and is then deflated and withdrawn. A plurality of straight endobiliary tubes or stents are then endoscopically implanted across the pseudocyst and stomach perforations to allow the contents of the pseudocyst to drain into the stomach, said biliary tubes or stents being arranged in a side-by-side fashion and being implanted one at a time. The endoscope is then removed from the patient. When drainage is complete (typically within a few weeks), the endoscope is reintroduced into the patient, and the biliary tubes or stents are withdrawn from the patient through the endoscope using a snare.

Although the aforementioned endoscopic approach has certain advantages over the surgical approach described above, the foregoing endoscopic approach still suffers from certain drawbacks. The procedural sequence may involve up to five separate instruments, exchanged through a gastroscope to complete the procedure, making the procedure complex and time consuming.

SUMMARY

The disclosure is directed to several alternative designs, materials and methods of manufacturing medical device structures and assemblies.

In a first example, a stent delivery system may comprise, a catheter shaft comprising an inner tubular member and an outer tubular member, the catheter shaft extending from a proximal end to a distal end, an inflatable balloon having a proximal end affixed to the outer tubular member of the catheter shaft and a distal end affixed to the inner tubular member of the catheter shaft proximal to the distal end of the catheter shaft, the inflatable balloon disposed adjacent to the distal end of the catheter shaft, a cutting electrode positioned at the distal end of the catheter shaft, a first heating electrode disposed about the inner tubular member of the catheter shaft and within an inner region of the inflatable balloon, a control console in electrical communication with each of the first cutting electrode and the second heating electrode, and a stent disposed about an outer surface of the inflatable balloon, the stent having a first collapsed configuration and a second expanded configuration.

Alternatively or additionally to any of the examples above, in another example, the stent may comprise a shape memory polymer.

Alternatively or additionally to any of the examples above, in another example, the cutting electrode may be disposed about the inner tubular member of the catheter shaft.

Alternatively or additionally to any of the examples above, in another example, a heat shrink tube may be disposed over the cutting electrode.

Alternatively or additionally to any of the examples above, in another example, the cutting electrode and the first heating electrode may be in electrical communication with the control console through separate electrical circuits.

Alternatively or additionally to any of the examples above, in another example, the cutting electrode may be configured to be operated in a first cutting mode and the first heating electrode may be configured to be operated in a second heating mode.

Alternatively or additionally to any of the examples above, in another example, a second heating electrode may be disposed about the inner tubular member of the catheter shaft and within the inner region of the inflatable balloon.

Alternatively or additionally to any of the examples above, in another example, the expanded configuration of the stent may include a proximal retention feature and a distal retention feature.

Alternatively or additionally to any of the examples above, in another example, the proximal retention feature may comprise a flared proximal end and the distal retention feature comprises a flared distal end.

Alternatively or additionally to any of the examples above, in another example, the stent may be cross-linked in the first collapsed configuration.

Alternatively or additionally to any of the examples above, in another example, the inflatable balloon may comprise a dumbbell shape in an inflated state.

Alternatively or additionally to any of the examples above, in another example, the second expanded configuration of the stent may generally correspond to the dumbbell shape of the inflatable balloon.

Alternatively or additionally to any of the examples above, in another example, the proximal retention feature may comprise an inwardly facing flare and the distal retention feature comprises an inwardly facing flare.

Alternatively or additionally to any of the examples above, in another example, the stent may be cross-linked in the second expanded configuration.

Alternatively or additionally to any of the examples above, in another example, the cutting electrode may comprise an annular ring.

Alternatively or additionally to any of the examples above, in another example, a stent delivery system may comprise a catheter shaft comprising an inner tubular member and an outer tubular member, the catheter shaft extending from a proximal end to a distal end, an inflatable balloon having a proximal end affixed to the outer tubular member of the catheter shaft and a distal end affixed to the inner tubular member of the catheter shaft proximal to the distal end of the catheter shaft, the inflatable balloon disposed adjacent to the distal end of the catheter shaft, a cutting electrode positioned at the distal end of the catheter shaft, a first heating electrode disposed about the inner tubular member of the catheter shaft and within an inner region of the inflatable balloon, a control console in electrical communication with each of the cutting electrode and the second electrode, a stent disposed about an outer surface of the inflatable balloon, the stent having a first collapsed configuration and a second expanded configuration.

Alternatively or additionally to any of the examples above, in another example, the cutting electrode may be disposed about the inner tubular member of the catheter shaft.

Alternatively or additionally to any of the examples above, in another example, a heat shrink tube may be disposed over the cutting electrode.

Alternatively or additionally to any of the examples above, in another example, the cutting electrode and the first heating electrode may be in electrical communication with the control console through separate electrical circuits.

Alternatively or additionally to any of the examples above, in another example, the cutting electrode may be configured to be operated in a first cutting mode and the first heating electrode may be configured to be operated in a second heating mode.

Alternatively or additionally to any of the examples above, in another example, the stent may comprise a shape memory polymer.

Alternatively or additionally to any of the examples above, in another example, the stent may be cross-linked in the first collapsed configuration.

Alternatively or additionally to any of the examples above, in another example, the stent may be cross-linked in the second expanded configuration.

Alternatively or additionally to any of the examples above, in another example, the second expanded configuration of the stent may include a flared proximal end region and a flared distal end region.

Alternatively or additionally to any of the examples above, in another example, the inflatable balloon may comprise a dumbbell shape in an inflated state.

Alternatively or additionally to any of the examples above, in another example, a second heating electrode may be disposed about the inner tubular member of the catheter shaft and within the inner region of the inflatable balloon.

Alternatively or additionally to any of the examples above, in another example, a stent delivery system may comprise a catheter shaft comprising an inner tubular member and an outer tubular member, the catheter shaft extending from a proximal end to a distal end, an inflatable balloon having a proximal end affixed to the outer tubular member of the catheter shaft and a distal end affixed to the inner tubular member of the catheter shaft proximal to the distal end of the catheter shaft, the inflatable balloon disposed adjacent to the distal end of the catheter shaft, a first cutting electrode positioned at the distal end of the catheter shaft, a second electrode disposed about the inner tubular member and within an inner region of the inflatable balloon, a control console in electrical communication with each of the first electrode and the second electrode, and a self expanding stent disposed about the outer surface of the inflatable balloon, the stent having a first collapsed configuration and a second expanded configuration, wherein an outer diameter of the inflatable balloon varies from the proximal end to the distal end thereof.

Alternatively or additionally to any of the examples above, in another example, the inflatable balloon may have a first region having a first outer diameter, a second region having a second diameter, and a third region having a third diameter, the second diameter smaller than the first and third diameters.

Alternatively or additionally to any of the examples above, in another example, the first region may be positioned adjacent and distal to the proximal end of the inflatable balloon, the third region may be positioned adjacent and proximal to the distal end of the inflatable balloon, and the second region may be positioned between the first and third regions.

Alternatively or additionally to any of the examples above, in another example, the stent may comprise a shape memory polymer.

Alternatively or additionally to any of the examples above, in another example, the stent may be cross-linked in the first collapsed configuration.

Alternatively or additionally to any of the examples above, in another example, a method for delivering a stent from a first body lumen to a second body lumen through adjacent opposing luminal wall may comprise advancing a gastroscope having a working channel to a target location near a lumen wall of the first body lumen, advancing a stent delivery system through the working channel of the gastroscope, the stent delivery system may comprise: a catheter shaft having a proximal end and a distal end, an inflatable balloon having an inner region and an outer surface, the inflatable balloon disposed adjacent to the distal end of the catheter shaft, a first cutting electrode positioned at the distal end of the catheter shaft, a second heating electrode disposed within the inner region of the inflatable balloon, a control console in electrical communication with each of the first cutting electrode and the second heating electrode, and a shape memory polymer stent disposed about the outer surface of the inflatable balloon, the stent transformable from a collapsed state to an expanded state, contacting the lumen wall of the first body lumen with the first cutting electrode, supplying an electrical current to the first cutting electrode to create an opening in the first body lumen, contacting a lumen wall of the second body lumen with the first cutting electrode, supplying an electrical current to the first cutting electrode to create an opening in the second body lumen, disposing the inflatable balloon within the opening in the first body lumen and the opening in the second body lumen, inflating the inflatable balloon, and heating an inflation fluid within the inflatable balloon to transform the stent from the collapsed state to the expanded state within the opening in the first body lumen and the opening in the second body lumen.

Alternatively or additionally to any of the examples above, in another example, inflating the inflatable balloon may comprise pre-inflating the inflatable balloon to a first pressure prior to heating the inflation fluid.

Alternatively or additionally to any of the examples above, in another example, inflating the inflatable balloon further may comprise inflating the inflatable balloon to a second pressure greater than the first pressure after heating the inflation fluid.

Alternatively or additionally to any of the examples above, in another example, heating the inflation fluid within the inflatable balloon may comprise supplying an electrical current to the second heating electrode.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
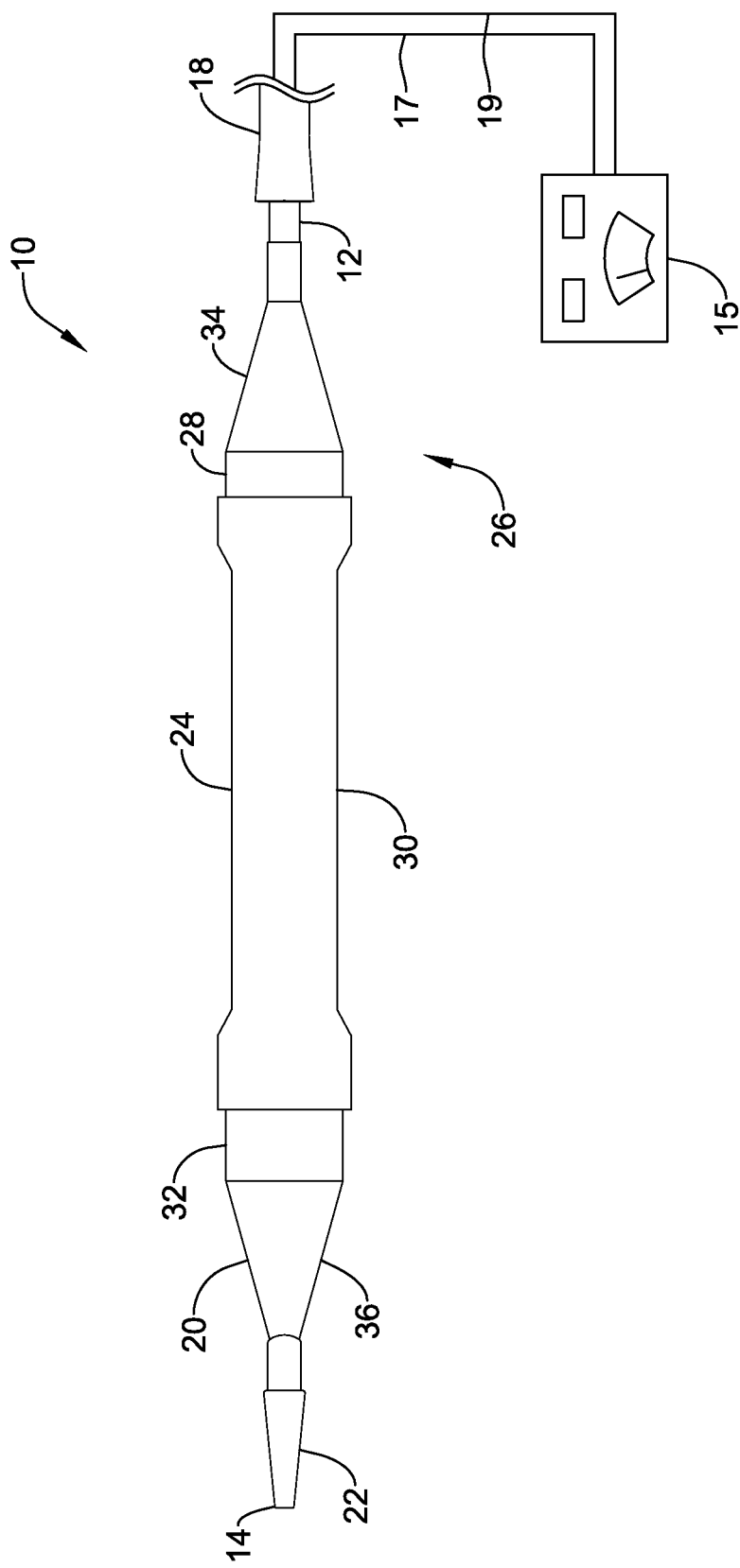
FIG. 1 is a side view of a distal end region of an illustrative stent delivery system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

A gastric or pancreatic pseudocyst is an aggregation of tissue, fluid, debris, pancreatic enzymes and blood that often develops in the peritoneal cavity after the onset of acute pancreatitis. Although many pseudocysts resolve themselves spontaneously, some pseudocysts become quite large and require treatment due to the unwanted pressure they exert against the stomach and/or neighboring organs. In some instances, it may be desirable to create an opening in the pseudocyst and the adjacent gastrointestinal tract and place a drainage stent therebetween to allow the pseudocyst to drain into the gastrointestinal tract. A single catheter device may be used to create an incision through a gastric structure (such as the stomach or duodenum) and the pseudocyst, dilate the incision, and place a large diameter stent within the incision. While the devices and methods described herein are discussed relative to pseudocyst drainage, it is contemplated that the devices and methods may be used in other locations and/or applications where placement of a stent is desired.

FIG. 1 is a side view of a distal end region of an illustrative stent delivery system 10. The stent delivery system 10 may include an elongate catheter shaft 12 having a proximal end (not shown) and a distal end 14. The catheter shaft 12 may extend proximally from the distal end 14 to the proximal end which is configured to remain outside of a patient's body. Although not shown, the proximal end of the catheter shaft 12 may include a hub attached thereto for connecting other treatment devices or providing a port for facilitating other treatments. The distal end 14 may include an introducer tip 22. It is contemplated that the stiffness and size of the catheter shaft 12 may be modified to form a delivery system 10 for use in various locations within the body. The catheter shaft 12 may further define a lumen 16 (shown in FIG. 2) through which a guidewire (not explicitly shown) may be passed in order to advance the catheter to a predetermined position, although this is not required. The stent delivery system 10 may be configured to be advanced through a working channel of an endoscope, gastroscope or other guide means 18.

The stent delivery system 10 may further include an inflatable balloon 20 affixed adjacent to a distal end region 26 of the catheter shaft 12. An expandable stent 24 may be disposed over the balloon 20. As will be discussed in more detail below, the shape of the expanded balloon 20 may be customized to achieve a desired shape of the expanded stent 24, although this is not required. In some instances, the outer diameter of the balloon 20 in an inflated configuration may vary over the length of the balloon 20. For example, the balloon 20 may include a first region 28 having a first outer diameter, a second region 30 having a second outer diameter, and a third region 32 having a third outer diameter. In some instances, the first and third regions 28, 32 may have larger diameters than the second intermediate region 30. This may create a balloon 20 having generally enlarged regions adjacent the proximal end region 34 and the distal end region 36 with a reduced diameter portion in an intermediate region 30 therebetween or a having a generally dumbbell shape.

Figure 2:
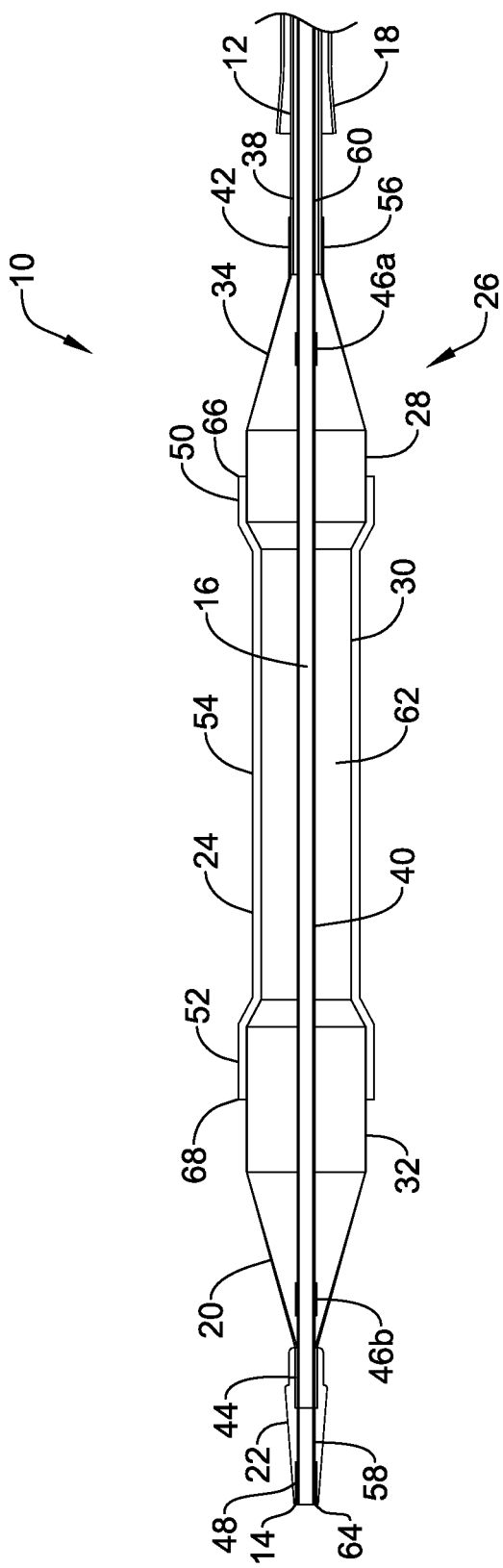
FIG. 2 is a cross-sectional view of the illustrative stent delivery system of FIG. 1.

FIG. 2 illustrates a cross-sectional view of the distal end region of the illustrative stent delivery system 10 of FIG. 1. The catheter shaft 12 may include an outer tubular member 38 and an inner tubular member 40. A proximal waist 42 of the balloon 20 may be secured to a distal end region 56 of the outer tubular member 38. A distal waist 44 of the balloon 20 may be secured to a distal end region 58 of the inner tubular member 40. The inner tubular member 40 may extend distally beyond the distal waist 44 of the balloon 20. In some instances, an annular inflation lumen 60 may be disposed between the outer tubular member 38 and the inner tubular member 40. The inflation lumen 60 may allow inflation fluid to pass from an inflation fluid source configured to remain outside the body to the interior region 62 of the balloon 20.

The stent delivery system 10 may further include one or more heating electrodes 46a, 46b (collectively referred to hereinafter as 46) disposed about the inner tubular member 40. While the system 10 is illustrated as including two heating electrodes 46, it is contemplated that the system 10 may include any number of heating electrodes 46 desired, such as, but not limited to one, two, three, four, or more. The electrodes 46 may be configured to receive radiofrequency (RF) energy from an RF generation console or control console 15 configured to remain outside the body to heat the inflation fluid within the interior region 62 of the balloon 20 using an applied voltage such as, but not limited to a continuous, discontinuous, intermittent, or pulsed voltage. In some instances, an algorithm may be used to control the voltage applied. In some instances, the voltage applied to the electrodes 46 may be different (e.g. less than or greater than) from the voltage applied to the cutting electrode 48. In some embodiments, a continuous lower voltage algorithm may be used to facilitate deployment of the stent 24. The electrodes 46 may be connected to the RF generation console through one or more electrical conductors 17, such as, but not limited to the copper lead of a copper-constantan thermocouple (T/C). In some instances, the electrodes 46a, 46b may be connected to the RF generation console such that they may be individually controlled. In other instances, the electrodes 46 may be simultaneously controlled. It is further contemplated that the inflation fluid may be heated by other means including application of thermal, ultrasound, laser, microwave, and other related energy sources and these devices may require that power be supplied by the generator in a different form.

The balloon 20 may further include an expandable stent 24 disposed about an outer surface of the balloon 20. The stent 24 may be expandable from a first collapsed configuration (not shown) to a second expanded configuration. The stent 24 may be structured to extend between a pancreatic pseudocyst and the gastrointestinal tract to allow for drainage of the pseudocyst. In some instances, in the expanded configuration, the stent 24 may include retention features or anti-migration flares 50, 52 positioned adjacent to the proximal end 66 and the distal end 68 of the stent 24. The anti-migration flares 50, 52 may be configured to engage an interior portion the walls of the pseudocyst or the gastric structure. In some embodiments, the retention features 50, 52 may have a larger diameter than an intermediate portion 54 of the stent 24 to prevent the stent 24 from migrating once placed between the pseudocyst and the gastrointestinal tract. It is contemplated that the retention features 50, 52 may have a larger cross-sectional area than the incision in the pseudocyst wall or the wall of the gastric structure.

In some embodiments, the stent 24 may be a self expanding stent formed from a shape memory polymer (SMP). However, it is contemplated that the stent 24 may be formed from any material desired. In broad terms, shape memory polymers behave similarly to shape memory alloys such as the nickel-titanium alloys commonly referred to as Nitinol. Shape memory polymers may be formed in a parent (or remembered) shape. The shape memory polymer may be temporarily deformed into another shape by heating the polymer above the transition temperature (in some instances this may be the glass transition temperature or the melting temperature), changing the shape of the polymer, and cooling the polymer while maintaining it in the temporary shape. An external stimulus, such as, but not limited to, heat, may be used to return the shape memory polymer to the remembered shape from the temporary shape. The shape memory polymer may be selected to be biocompatible and/or bioabsorbable. A bioabsorbable stent may be designed to completely drain the pseudocyst and then deteriorate soon after which may eliminate the need for a removal procedure. In some instances, the stent 24 may be formed from polycyclooctene. In other instances, a blend of polycyclooctene and poly(styrene-butadiene-styrene) (SBS) may be utilized. These are just examples. It is contemplated that the stent 24 may be formed or cross-linked in either the desired expanded configuration or in a generally collapsed configuration. The stent 24 may be formed to have generally solid walls. This may prevent tissue in-growth as well as facilitate removal of the stent 24. In some instances, a SMP stent may also offer high crush resistance allowing a single stent to be used. It is contemplated that the stent 24 may be compressed and/or elongated into a small enough diameter to fit through the lumen of the gastroscope 18 while also being capable of expanding to a large enough diameter, up to 18 French (6 millimeters) or more, such that a single stent 24 may provide the desired drainage.

In some embodiments, the stent 24 may be formed or cross-linked in its collapsed or unexpanded shape making this the remembered shape. The unexpanded stent 24 may then be loaded over the uninflated balloon 20 (not explicitly shown), which may then be brought through the working channel of a gastroscope 18. Once the loaded balloon 20 is clear of the gastroscope 18, it may be positioned in the correct location relative to the pseudocyst. The balloon 20 may then be filled with saline or other inflation fluid and heated using heating electrodes 46. When heated above a critical transition temperature value, the SMP material becomes malleable. As the balloon 20 is inflated under the heated SMP material, the stent 24 may expand with the balloon 20, thus taking on the shape of the balloon 20. For example, the enlarged first and third regions 28, 32 of the balloon 20 may form anti-migration flares 50, 52 while the intermediate region 30 of the balloon 20 may form a large diameter lumen configured to be positioned between the pseudocyst and the gastric structure. While the balloon 20 remains inflated, the heating source may be turned off, allowing the balloon 20, stent 24 and inflation fluid to cool. Once the stent 24 has cooled, it may become stiff and retain its temporary or deformed shape. The balloon 20 may then be deflated and removed, leaving the expanded stent 24 in the correct drainage location, as will be discussed in more detail with respect to FIGS. 3A-3F. It is contemplated that stents formed in the unexpanded configuration may be reshaped using different size balloons allowing the shape of the expanded stent to be customized to a desired application. It is contemplated that the stent 24 may be removed using the reverse of the placement process. For example, the deflated balloon 20 may be brought through the gastroscope 18 and then placed in the center of the expanded stent 24. The balloon 20 may be inflated with an inflation fluid, so that the outer surface of the balloon 20 contacts an inner surface of the stent 24. The balloon may be heated using, for example, heating electrodes 46 and resultantly heating the stent 24. The stent 24 may return to its malleable state. The balloon 20 may then be deflated. Since the remembered shape of the stent 24 is the unexpanded size, it reverts back to its original state as the balloon 20 is deflated. The stent 24 once again fits over the balloon 20, and can be removed by pulling the whole device through the gastroscope 18.

In other embodiments, the stent 24 may alternatively be formed by injection molding SMP material in the expanded configuration, with a large diameter and anti-migration features. The stent 24 may be cross-linked in this state, meaning that the expanded configuration is the remembered shape of the stent 24. The stent 24 may be heated and compressed over an uninflated balloon 20 (not explicitly shown), such that it fits through the working channel of a gastroscope 18. In some instances, the stent 24 may be stretched along its longitudinal axis and radially compressed about the balloon 20 such that the collapsed delivery configuration has a longer length and smaller cross-section than the expanded configuration. Stretching the stent 24 along its longitudinal axis may reduce the diameter of the stent 24 more than would occur if the stent 24 were only radially compressed. It is contemplated that this may allow more material to be used in forming the stent 24. Longitudinal stretching and/or radial compression may allow the anti-migration features 50, 52 to flatten and for the stent 24 to become sufficiently small to pass through the gastroscope 18. Once the balloon 20 passes completely through the gastroscope 18, and is placed in the correct deployment location, the balloon 20 may be inflated with an inflation fluid and heated above the transition temperature of the SMP, using, for example, heating electrodes 46. The SMP material may become malleable when heated and revert to its predetermined shape (which it was set to by cross linking before the stent 24 was compressed onto the balloon 20). The stent 24 is then cooled by allowing the balloon 20 to cool. The balloon 20 is then deflated and the device 10 is removed through the gastroscope 18, leaving the stent 24 expanded and in the correct position. It is contemplated that when the stent 24 is cross-linked in the expanded configuration, the balloon 20 used to deploy the stent 24 may be straight or have a relatively constant diameter over the first region 28, the second region 30, and the third region 32. It is further contemplated that the stent 24 may be removed using the reverse of the placement process. The deflated balloon 20 may be brought through the gastroscope 18 and then placed in the center of the expanded stent 24. The balloon 20 may be inflated with an inflation fluid, so that the outer surface of the balloon 20 contacts an inner surface of the stent 24. The balloon 20 may be heated using, for example, heating electrodes 46 and resultantly heating the stent 24. The stent 24 may return to its malleable state. A retrieval sheath (not shown) or other retrieval mechanism may be utilized to compress the stent 24 into a size and shape suitable for removal. The balloon 20 may then be deflated and allowed to cool. The stent 24 may once again fit over the balloon 20, and can be removed by pulling the whole device through the gastroscope 18.

A cutting electrode 48 may be disposed about the inner tubular member 40 adjacent the distal end 14 of the catheter shaft 12. The cutting electrode 48 may be an annular ring having an inner diameter similar to an outer diameter of the inner tubular member 40. A distal end 64 of the cutting electrode 48 may generally align with the distal end 14 of the catheter shaft 12 such that only the distal edge of the cutting electrode 48 is exposed. The introducer tip 22 may be heat shrunk over the cutting electrode 48 and the distal end region 58 of the inner tubular member 40 to insulate the cutting electrode 48 as well as to dilate an opening formed by the cutting electrode 48. It is contemplated that the introducer tip 22 may be tapered to allow the distal edge of the cutting electrode 48 to be exposed while also insulating the remaining portion of the electrode 48. In some embodiments, the cutting electrode 48 may be a 316 stainless steel ring. It is contemplated that, in some instances, the electrode 48 may be a radiopaque marker ring or may include radiopaque properties. The electrode 48 may be configured to receive radiofrequency (RF) energy from an RF generation console or control console 15 to create an incision in a body tissue using a pulsed high voltage RF algorithm. The cutting electrode 48 may be operated in a monopolar mode with a grounding electrode provided on the skin of the patient to provide a return grounding path for the RF energy. The electrode 48 may be connected to the console through one or more electrical conductors 19, such as, but not limited to the copper lead of a copper-constantan thermocouple (T/C). It is contemplated that the cutting electrode 48 may be in communication with the same RF generation console as the heating electrodes 46, although this is not required. When so provided, a single RF generation system may be configured to effect the cutting operation independently of the heating operation with the addition of a second set of control parameters and separate electrical circuits. It is contemplated that the RF generation console may be custom built for this application, or could be a standard clinical system. It is further contemplated that the incision may be created by other means including application of thermal, ultrasound, laser, microwave, and other related energy sources and these devices may require that power be supplied by the generator in a different form.

The cutting electrode 48 may allow the stent delivery system 10 to create an incision through the gastric structure and the pseudocyst without withdrawal or exchange of devices which may save time and reduce the number of devices required for this procedure. It is further contemplated that a mechanical blade or needle distal to the balloon may require the device to be protected during tracking through the scope and positioning, and mechanically extended beyond its protection to make the incision thus requiring additional devices and/or withdrawal of devices as the presence of the balloon prevents incorporation of mechanical protection and actuation means to effect this.

Figure 3A:
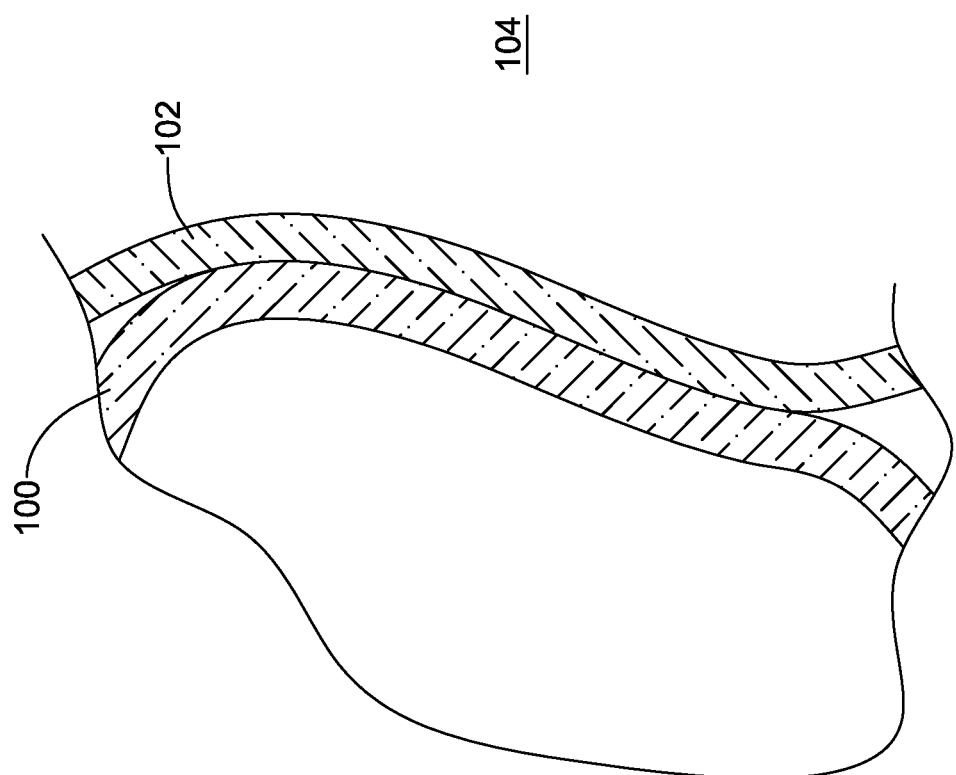
FIGS. 3A-3F are fragmentary schematic views illustrating how the stent delivery system of FIG. 1 may be used.
Figure 3B:
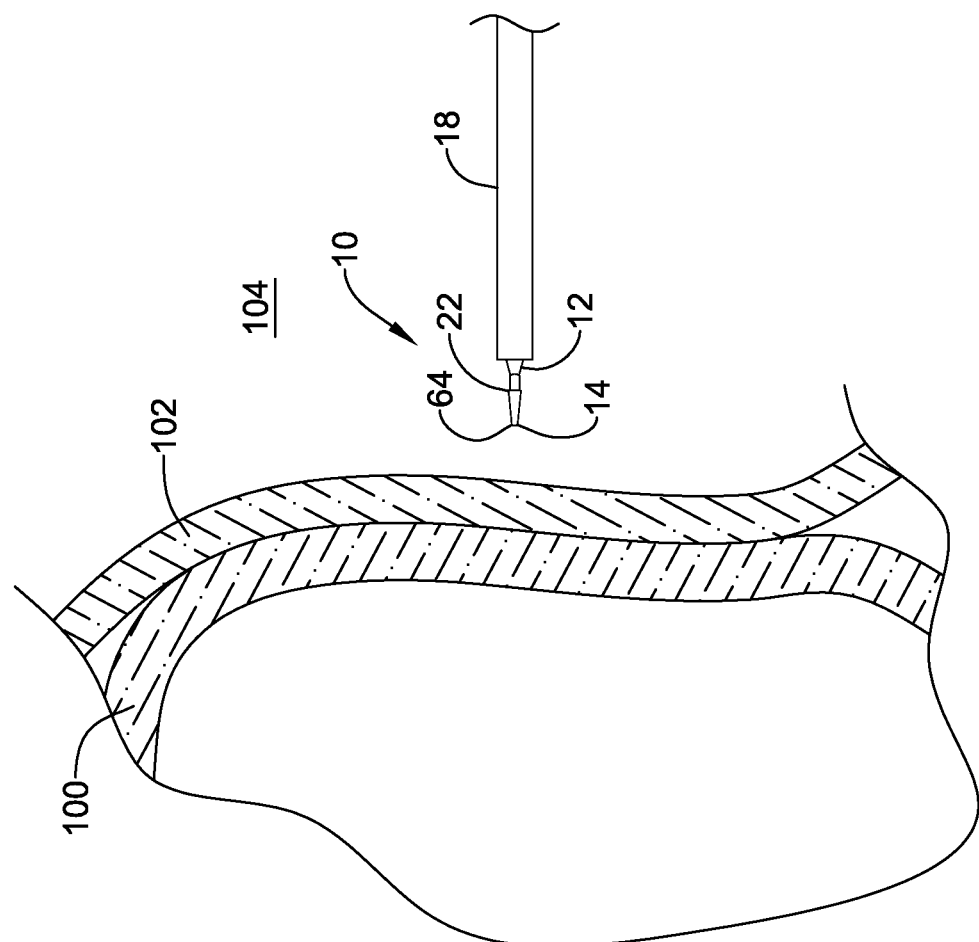

Referring now to FIGS. 3A-3F there is illustrated an illustrative method in which the system 10 may be used to drain a gastric pseudocyst. In FIG. 3A, a gastric pseudocyst 100 is shown pressing inwardly against the exterior surface of a wall 102 of the stomach 104. However, it is contemplated that the pseudocyst may be pressed up against other portions of the gastrointestinal tract. The patient may be prepped and a standard patient return ground pad applied adhesively to the patient. The gastroscope 18 may be advanced through the mouth of the patient and brought to a predetermined location adjacent a lumen wall within a first body lumen near the pseudocyst, as shown in FIG. 3B. The gastroscope 18 may be precisely located by visual observation of the distention caused in the stomach or duodenal wall by the pseudocyst and/or fluoroscopy. The stent delivery system 10 may be introduced through the working channel of the gastroscope. The distal tip 14 including the distal end 64 of the cutting electrode 48 may be positioned against the lumen wall or stomach wall 102. RF energy is applied to the cutting electrode 48 from the RF generator in a first cut mode using an applied voltage such as, but not limited to a continuous, discontinuous, intermittent, or pulsed voltage. In some instances, an algorithm may be used to control the voltage applied. In some instances, the voltage applied to the cutting electrode 48 be different (e.g. less than or greater than) from the voltage applied to the heating electrodes 46. For example, a pulsed high voltage algorithm may be used. The distal end 64 of the cutting electrode 48 may cut through the stomach wall 102 with light pressure applied on the catheter and subsequently come into contact with a second lumen wall or the pseudocyst 100 wall. With continued application of RF energy and light pressure applied on the catheter 12, the distal end 64 of the cutting electrode may cut through the second lumen wall or pseudocyst 100 to create an opening or incision 106 (shown in FIG. 3C) spanning from the stomach 104 to the pseudocyst 100. This may result in release of cyst contents into the gastrointestinal tract, where they may be aspirated. Patients qualifying for endoscopic drainage may have adherences between the pancreas and the adjacent gastric structure (stomach or duodenum) which prevents leakage of the pseudocyst material into the peritoneal cavity. Continued pressure on the tip begins the dilation process as the insulating tip 22 enters the incision caused by the RF cut.

Figure 3C:
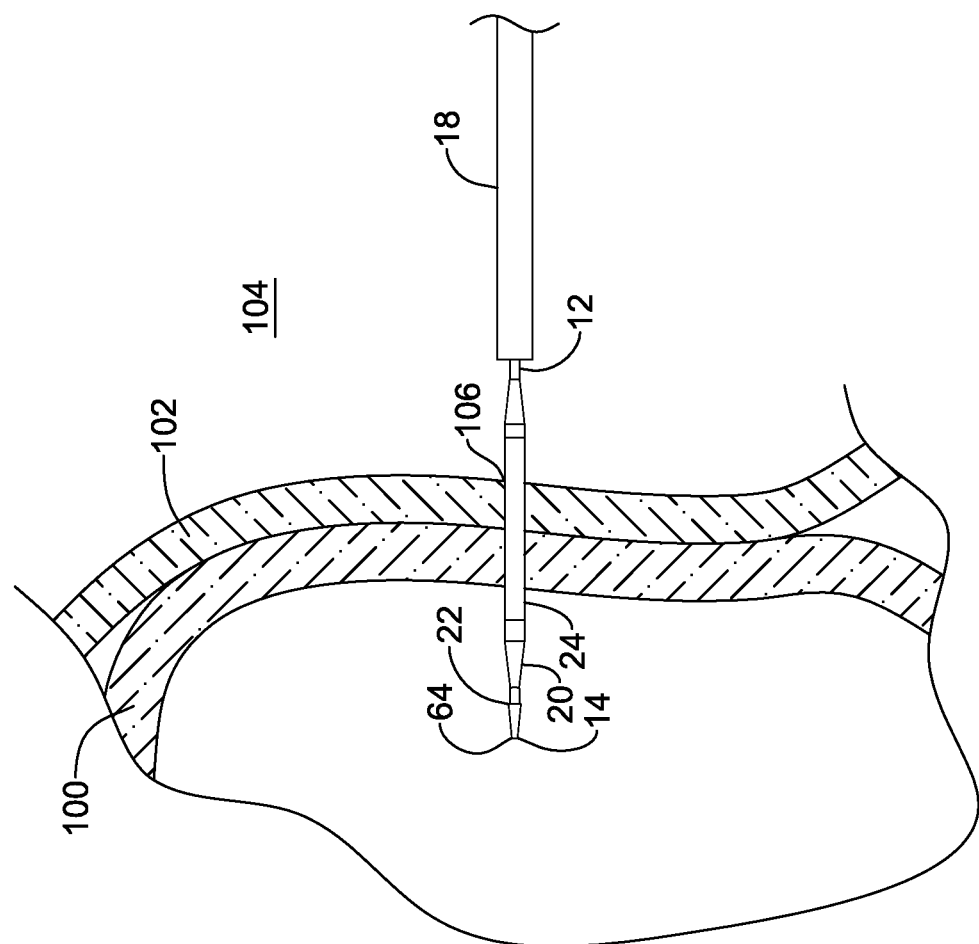
Figure 3D:
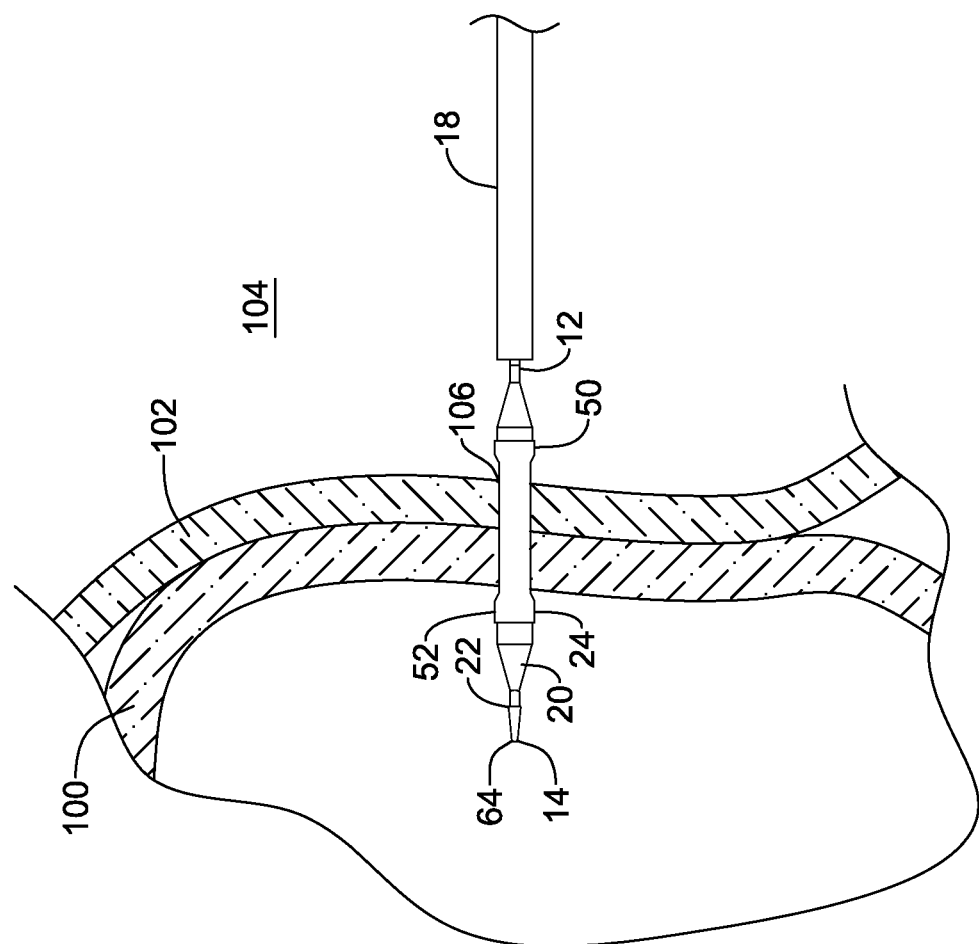

The catheter 12 may be advanced until the stent 24 is properly located in the pseudocyst 100 as illustrated in FIG. 3C. The stent 24 can incorporate radiopaque characteristics to facilitate verification of placement. The RF generator mode may be switched to a second heat mode for deployment of the stent 24. The balloon 20 may be slightly pre-inflated with inflation fluid to a first pressure (gauge pressure) of, for example, 2-4 atmospheres (atm) (202-405 kilopascals, kPa) and the heat mode actuated thus heating the inflation fluid in the balloon 20 by passing RF energy between the two heating electrodes 46a, 46b in a bipolar mode. The balloon 20 may be further inflated to a second pressure (gauge pressure) in the range of, for example, 10 atm (1013 kPa), adding inflation fluid as the indicated temperature approaches the desired target transition temperature. In some instances, a separate temperature sensor or thermocouple may be provided within the balloon 20 while in other instances the electrodes 46 may be used to measure the temperature of the inflation fluid. The stent 24 may expand in response to the heat and pressure until the balloon 20 is fully inflated, which may be indicated by stable pressure. Inflation of the balloon 20 may simultaneously dilate the incision 106 and expand the stent 24, as shown in FIG. 3D.

Figure 3E:
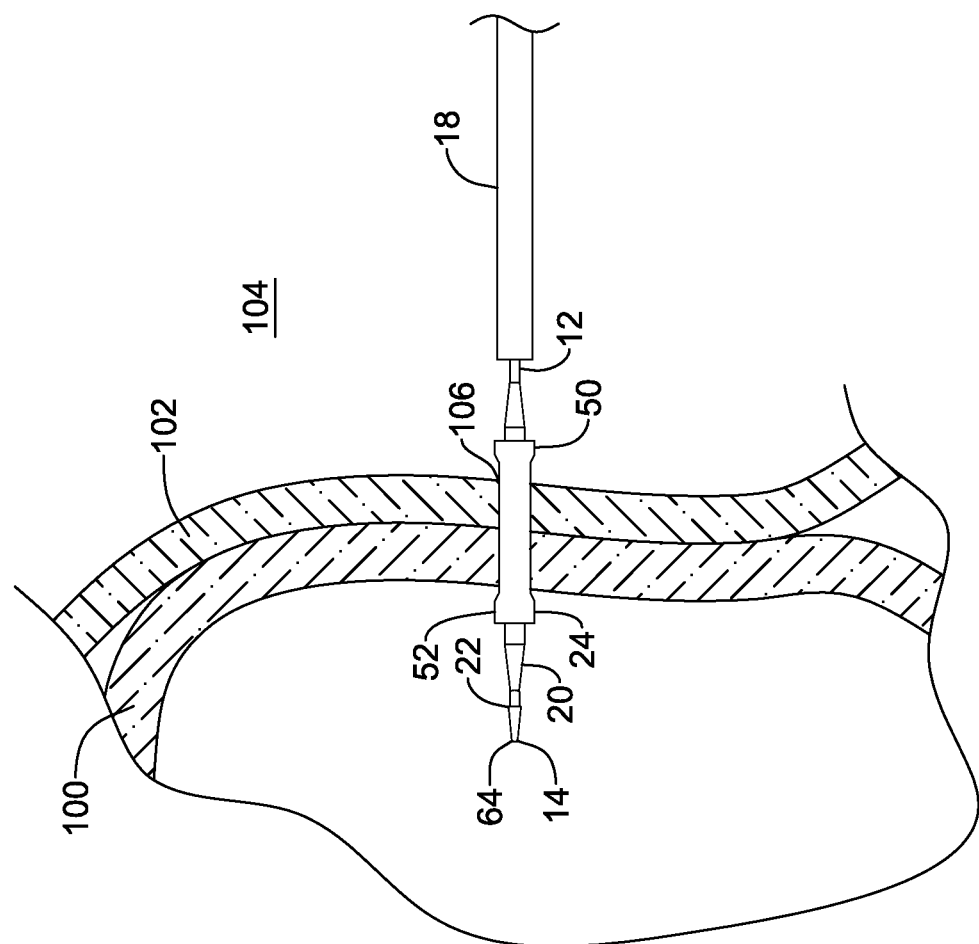
Figure 3F:
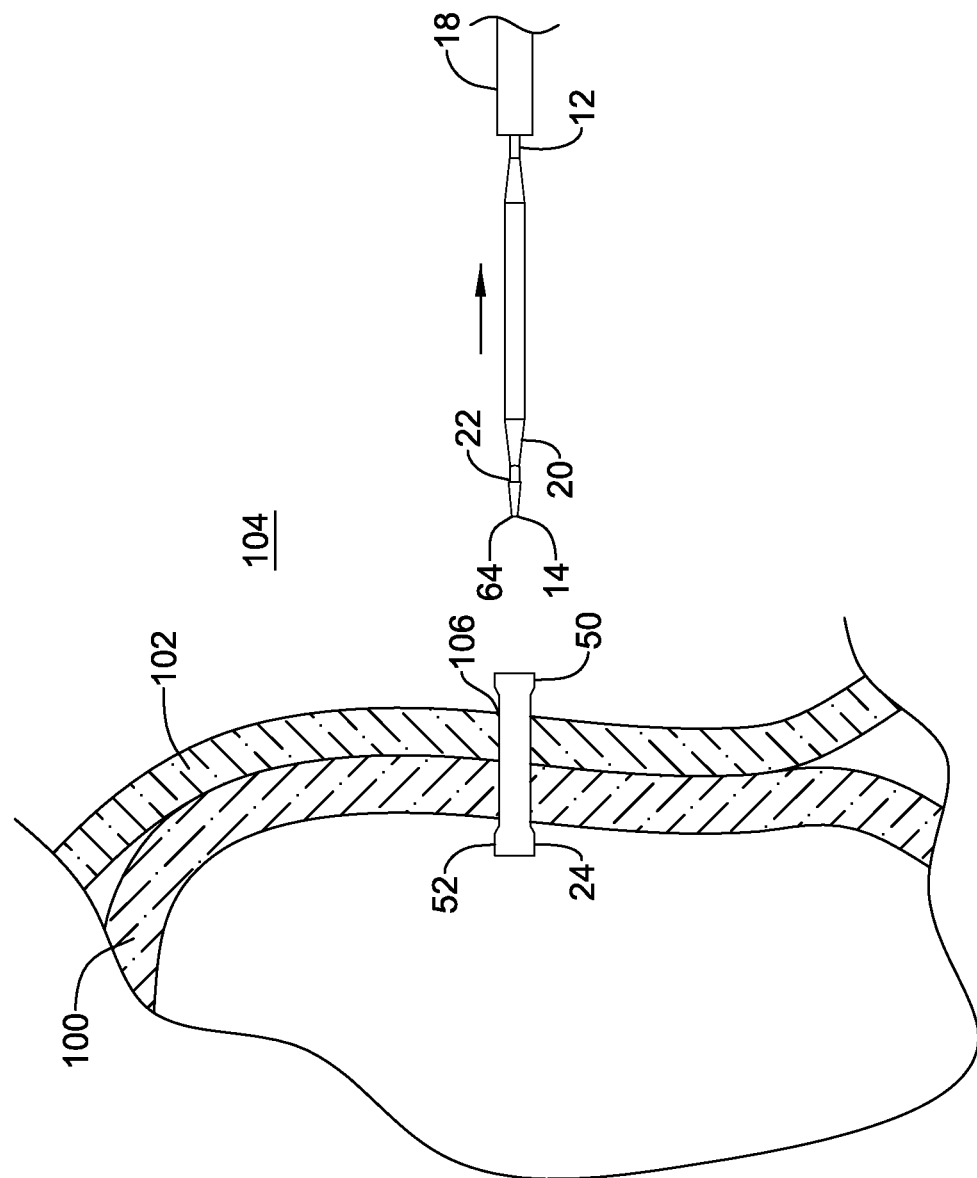

As discussed above, the stent 24 can be formed in either the expanded configuration or the collapsed configuration. When the stent 24 is formed in the expanded configuration, application of heat to the transition temperature will cause the stent 24 to regain its "remembered" expanded state. When the stent 24 is formed in the collapsed configuration, application of heat and pressure from the expanding balloon 20 will cause the stent 24 to be deformed into a "temporary" shape following the profile of the inflated balloon 20. The RF energy may be turned off and the system is allowed to cool to body temperature effectively "freezing" the stent 24 in its expanded state. The balloon 20 may be deflated while the stent 24 remains in the expanded configuration, as shown in FIG. 3E, to establish a drainage path from the pseudocyst 100 to the stomach 104 or gastrointestinal tract. As can be seen, a distal anti-migration flare 52 may be positioned within the pseudocyst and a proximal anti-migration flare 50 may be positioned with the stomach 104. The anti-migration flares 50, 52 may have a cross-sectional area larger than a cross-sectional area of the incision 106. This may prevent or help prevent the stent 24 from migrating into either the pseudocyst 100 or the stomach 104 once the stent 24 has been deployed. The catheter 12 may then be withdrawn through the gastroscope 18 as shown in FIG. 3F. It is contemplated that in some instances, the RF generator may include a manual control sequence. In other instances, the RF generator may include some automatic control sequences. For example, while each energy application (cut or heat mode) may be initiated manually, the energy termination may be manual or automatic.

Figure 4:
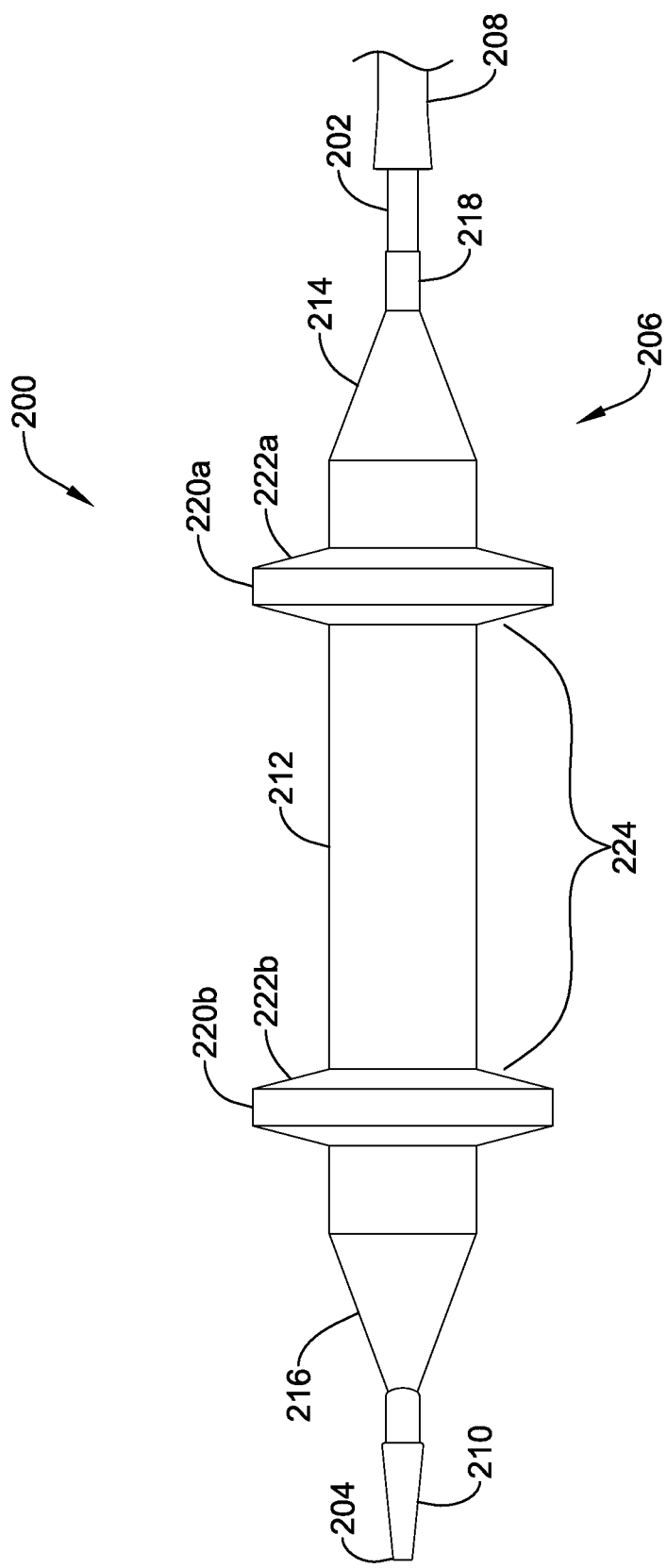
FIG. 4 is a side view of a distal end region of another illustrative stent delivery system.

FIG. 4 is a side view of a distal end region of another illustrative stent delivery system 200. The stent delivery system 200 may be similar in form and function to the stent delivery system 10 described above. The stent delivery system 200 may include an elongate catheter shaft 202 having a proximal end (not shown) and a distal end 204. The catheter shaft 202 may extend proximally from the distal end 204 to the proximal end which is configured to remain outside of a patient's body. Although not shown, the proximal end of the catheter shaft 202 may include a hub attached thereto for connecting other treatment devices or providing a port for facilitating other treatments. The distal end 204 may include an introducer tip 210. It is contemplated that the stiffness and size of the catheter shaft 202 may be modified to form a delivery system 200 for use in various locations within the body. The catheter shaft 202 may further define a lumen through which a guide wire (not explicitly shown) may be passed in order to advance the catheter to a predetermined position, although this is not required. The stent delivery system 200 may be configured to be advanced through a working channel of an endoscope, gastroscope or other guide means 208.

The stent delivery system 200 may further include an inflatable balloon 212 affixed adjacent to a distal end region 206 of the catheter shaft 202. The catheter shaft 202 may include an outer tubular member and an inner tubular member. A proximal waist 218 of the balloon 212 may be secured to a distal end region of the outer tubular member. A distal waist of the balloon 212 may be secured to a distal end region of the inner tubular member. The inner tubular member may extend distally beyond the distal waist of the balloon 212. In some instances, an annular inflation lumen may be disposed between the outer tubular member and the inner tubular member. The inflation lumen may allow inflation fluid to pass from an inflation fluid source configured to remain outside the body to the interior region of the balloon. While not explicitly shown, the stent delivery system 200 may further include one or more heating electrodes disposed within the balloon 212 and a cutting electrode disposed adjacent the distal end 204.

In some instances, the diameter of the balloon 212, in an inflated configuration, may vary over the length of the balloon 212. For example, the balloon 212 may include a proximal flared region 220a and a distal flared region 220b. The flared regions 220a. 220b may have a larger cross-sectional area than an intermediate region 224 disposed between the proximal flare 220a and the distal flare 220b. This may create a balloon 212 having generally enlarged regions adjacent the proximal end region 214 and the distal end region 216 with a reduced diameter portion in an intermediate region 224 therebetween or a having a generally dumbbell shape.

It is contemplated that the transition 222a, 222b from the cross-sectional area of the intermediate region 224 to the flared regions 220a. 220b may be gradual, sloped, or occur in an abrupt step-wise manner, as desired. The shape of the balloon 212 in the inflated state may be selected to mold a shape memory stent into a desired configuration. While not explicitly shown, an unexpanded shape memory stent may be loaded over the uninflated balloon 212. The stent delivery system 200 may then be brought through the working channel of a gastroscope 208. Once the loaded balloon 212 is clear of the gastroscope 208, it may be positioned in the correct location relative to the pseudocyst. The balloon 212 may filled with saline or other inflation fluid and heated using heating electrodes (not explicitly shown). When heated above a critical transition temperature value, the SMP material becomes malleable. As the balloon 212 is inflated under the heated SMP material, the stent may expand with the balloon 212, thus taking on the shape of the balloon 212. While the balloon 212 remains inflated, the heating source may be turned off, allowing the balloon 212, stent and inflation fluid to cool. Once the stent has cooled, it may become stiff and retain its shape. The balloon 212 may then be deflated and removed, leaving the expanded stent in the correct drainage location. The stent may have a length sufficient to be disposed over both the proximal flared region 220a and the distal flared region 220b of the balloon 212. When the stent is deployed, the flared regions 220a, 220b may create flared ends, or anti-migration features, in the stent. A first anti-migration feature may be positioned within the pseudocyst and a second anti-migration feature may be positioned within the gastrointestinal tract. It is contemplated that the size and shapes of the flared regions 220a, 220b and the intermediate region 224 may be selected to achieve a desired size and shape stent. For example, a length of the flared regions 220a, 220b along a longitudinal axis of the balloon 212 may be longer or shorter as desired. Other configurations are also contemplated.

Figure 5:
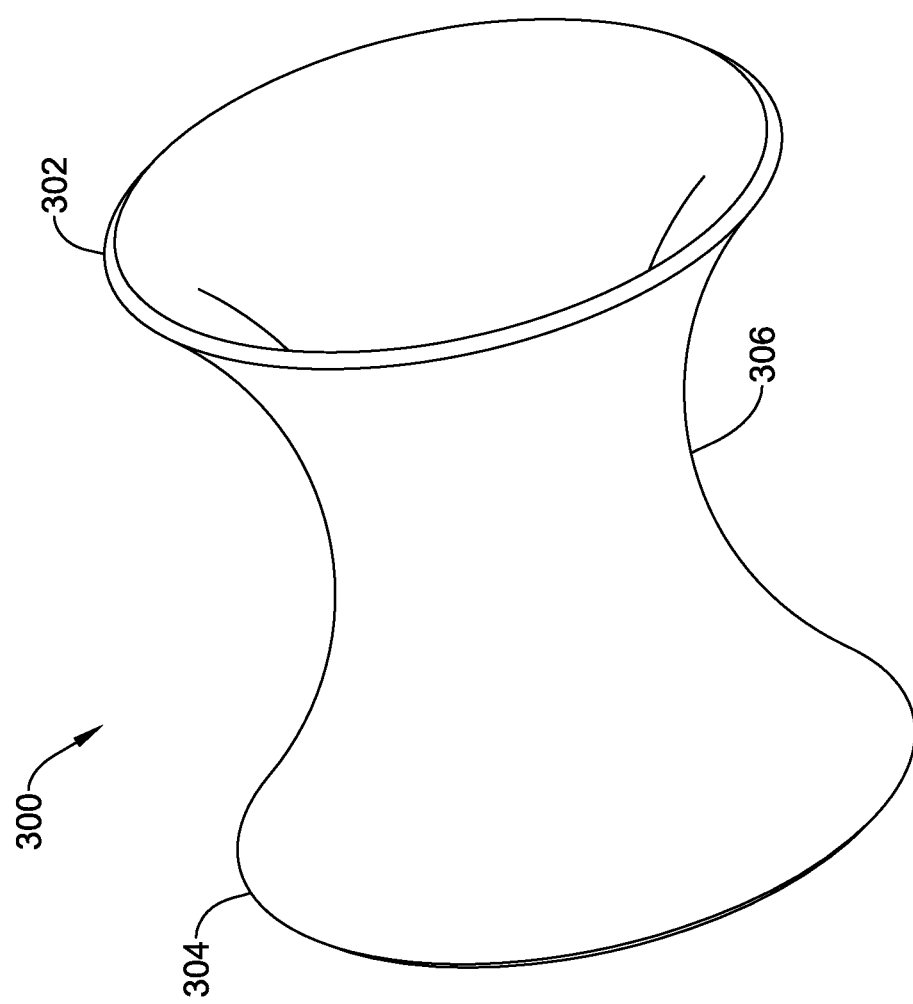
FIG. 5 is a perspective view of another illustrative stent.

As discussed above, a stent may be formed or cross-linked from a shape memory polymer in its unexpanded shape or its expanded shape, as desired. When the stent is formed in the unexpanded shape, the expanded stent may take on the shape of the delivery balloon, as described above. FIG. 5 illustrates another illustrative shape memory polymer stent 300 that may be cross-linked in the unexpanded shape or the expanded shape. The drainage stent 300 may include a flared proximal end 302, a flared distal end 304 and a large diameter intermediate region 306 such that the inner diameter of the stent 300 varies over the length of the stent 300. The proximal end 302 and the distal end 304 may be larger than the intermediate region 306 to prevent the drainage stent 300 from migrating once it has been deployed. When the stent 300 is cross-linked in an unexpanded, or generally tubular shape, a shaped deployment balloon, such as, but not limited to, balloons 20 or 212 may be utilized to achieve the desired expanded shape of the stent 300. While not explicitly shown, a deployment balloon may have a barbell or curved shape to achieve the shape of stent 300. It is further contemplated that stent 300 may be formed in the expanded configuration illustrated in FIG. 5. In such an instance, the stent 300 may be deployed using a "straight" balloon or one that does not include additional structural features (such as enlarged diameter portions) configured to change the shape of the expanded stent 300.

Figure 6:
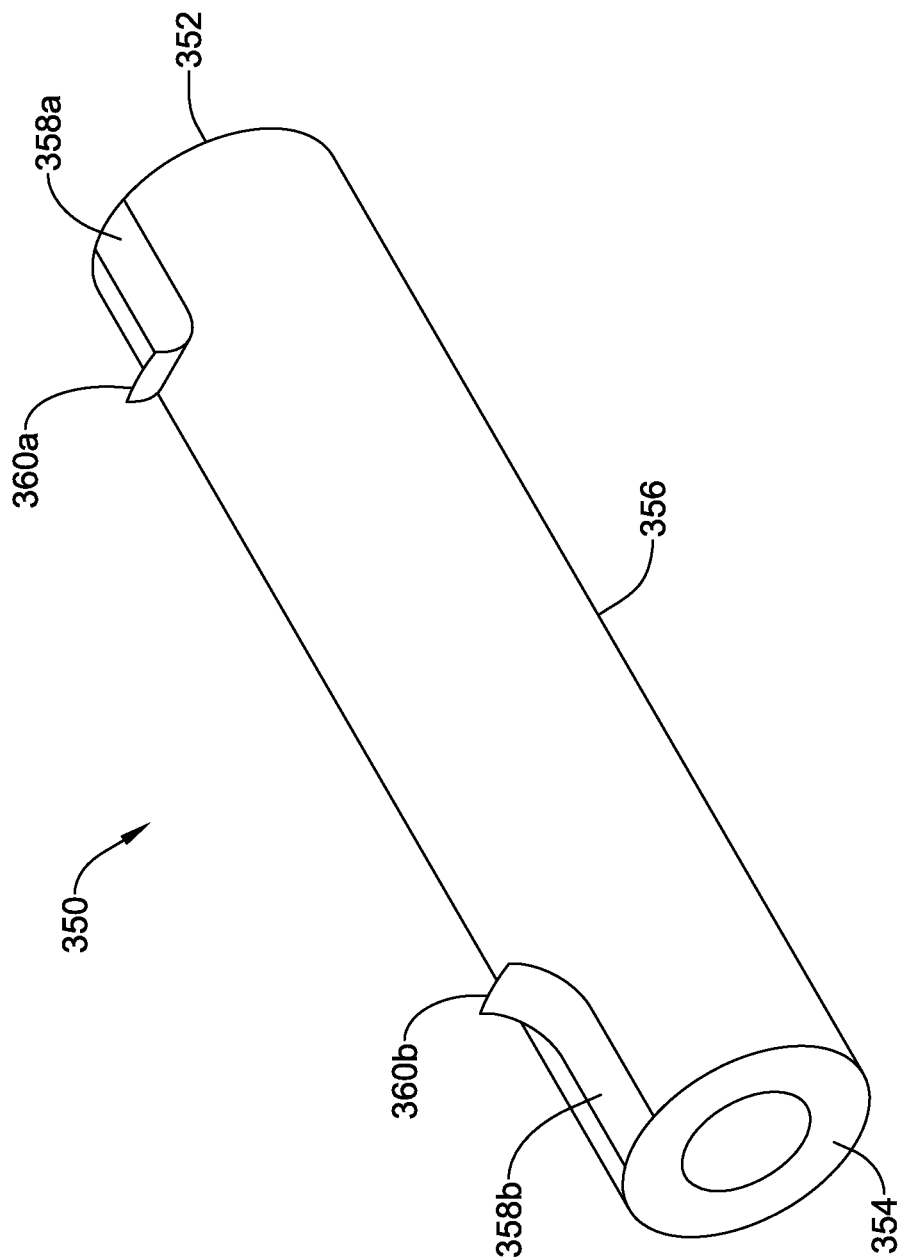
FIG. 6 is a perspective view of another illustrative stent.

FIG. 6 illustrates another illustrative stent 350. The stent 350 may be formed from a shape memory polymer. The stent 350 may be formed by injection molding SMP material. The stent 350 may be molded in its expanded configuration, with a large diameter and anti-migration features. The stent 350 may be cross-linked in this state, meaning that the expanded configuration is the remembered shape of the stent 350. The stent 350 may include a proximal end 352 and a distal end 354. The stent 350 may have a generally tubular intermediate region 356 extending between the proximal end 352 and the distal end 354. The inner diameter of the stent 350 may be generally constant or uniform from the proximal end 352 to the distal end 354. The stent 350 may further include a pair of retention features 358a, 358b positioned adjacent to the proximal and distal ends 352, 354. The retention features 358a, 358b may include inward facing barbs 360a, 360b. The barbs 360a, 360b may be sized and shaped to prevent the drainage stent 350 from migrating once it has been deployed between the pseudocyst and the gastrointestinal tract. The barbs 360a, 360b may be positioned on an outer surface of the stent 350. The stent 350 may be formed having the final expanded shape and heated and deformed to be loaded onto a delivery balloon. It is contemplated that the delivery balloon may be generally straight. During deployment of the stent 350, application of heat may cause the stent 350 to return to its remembered or expanded shape.

Figure 7:
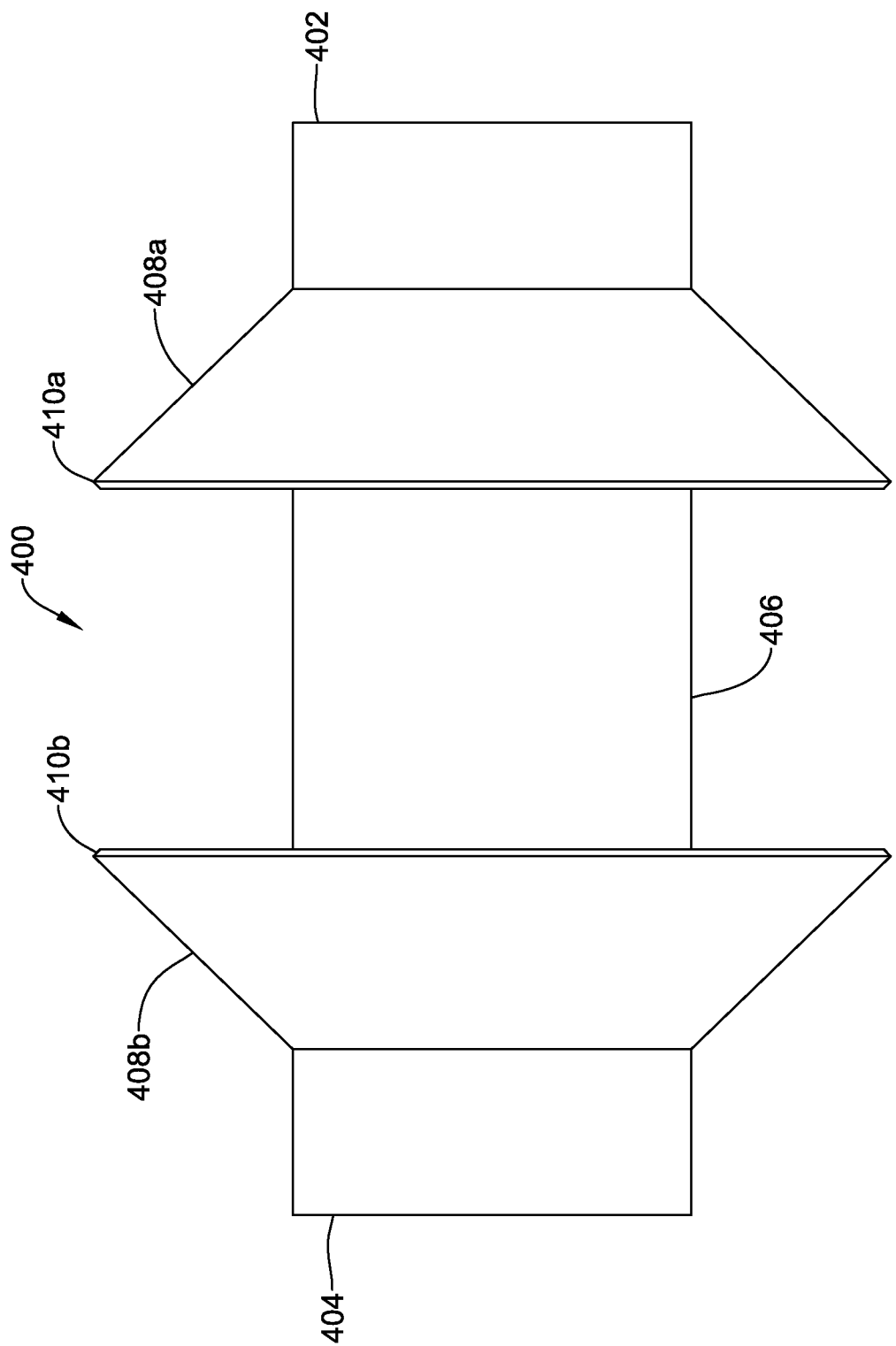
FIG. 7 is a perspective view of another illustrative stent.

FIG. 7 illustrates another illustrative self expanding stent 400. The stent 400 may be formed from a shape memory polymer. The stent 400 may be molded in its expanded configuration, with a large diameter and anti-migration features. The stent 400 may be cross-linked in this state, meaning that the expanded configuration is the remembered shape of the stent 400. The stent 400 may include a proximal end 402 and a distal end 404. The stent 400 may have a generally tubular intermediate region 406 extending between the proximal end 402 and the distal end 404. The stent 400 may further include a pair of retention features 408a, 408b positioned adjacent to the proximal and distal ends 402, 404. The inner diameter of the tubular intermediate portion 406 stent 400 may be generally constant or uniform from the proximal end 402 to the distal end 404 while an inner diameter of the retention features 408a, 408b may be larger than that of the intermediate portion 406. However, it is contemplated that the inner diameter of the intermediate portion 406 may vary over the length thereof. The retention features 408a, 408b may be inwardly facing flares. For example, the proximal retention feature 408a may increase in diameter from the proximal end 402 towards the distal end 404. The distal retention feature 408b may increase in diameter from the distal end 404 towards the proximal end 402. This may allow the largest portion 410a, 410b of the retention features 408a, 408b to be positioned against the walls of the pseudocyst or gastrointestinal tract when the stent 400 is deployed. The retention features 408a, 408b may be sized and shaped to prevent the drainage stent 400 from migrating once it has been deployed between the pseudocyst and the gastrointestinal tract. The retention features 408a, 408b may be positioned on an outer surface of the stent 400. The stent 400 may be formed having the final expanded shape and heated and deformed to be loaded onto a delivery balloon. It is contemplated that the delivery balloon may be generally straight. During deployment of the stent 400, application of heat may cause the stent 400 to return to its remembered or expanded shape.

Figure 8:
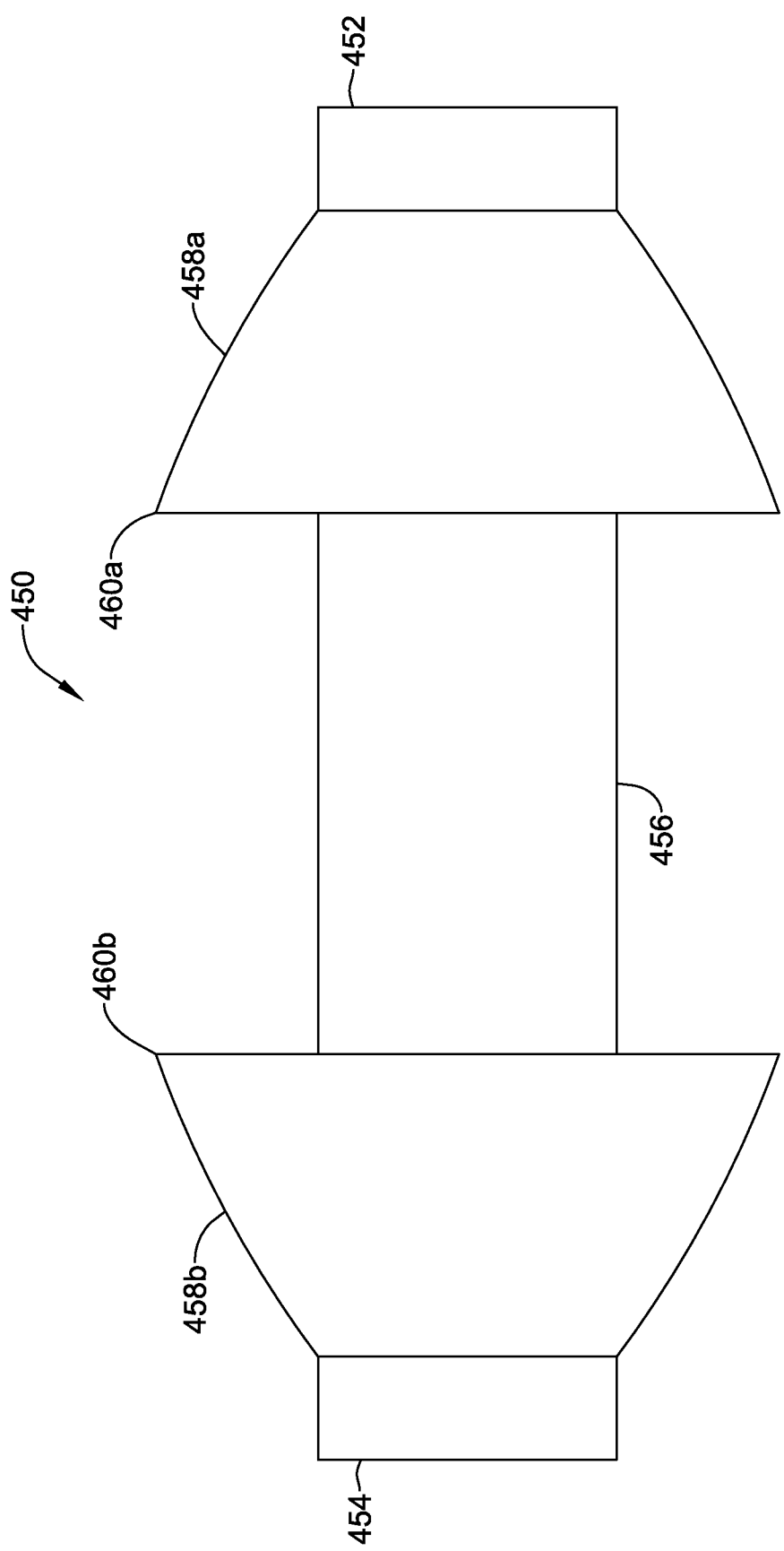
FIG. 8 is a perspective view of another illustrative stent.

FIG. 8 illustrates another illustrative self expanding stent 450. The stent 450 may be formed from a shape memory polymer. The stent 450 may be molded in its expanded configuration, with a large diameter and anti-migration features. The stent 450 may be cross-linked in this state, meaning that the expanded configuration is the remembered shape of the stent 450. The stent 450 may include a proximal end 452 and a distal end 454. The stent 450 may have a generally tubular intermediate region 456 extending between the proximal end 452 and the distal end 454. The stent 450 may further include a pair of retention features 458a, 458b positioned adjacent to the proximal and distal ends 452, 454. The inner diameter of the stent 450 may be generally constant or uniform from the proximal end 452 to the distal end 454 while an inner diameter of retention features 458a, 458b may be larger than that of the stent 450. However, it is contemplated that the inner diameter of the stent 450 may vary over the length thereof. The retention features 458a, 458b may be inwardly facing flares. In some instances, the retention features 458a, 458b may have a generally curved or cup-like profile. For example, the proximal retention feature 458a may increase in diameter in a curved manner from the proximal end 452 towards the distal end 454. The distal retention feature 458b may increase in diameter in a curved manner from the distal end 454 towards the proximal end 452. This may allow the largest portion 460a, 460b of the retention features 458a, 458b to be positioned against the walls of the pseudocyst or gastrointestinal tract when the stent 450 is deployed. The retention features 458a, 458b may be sized and shaped to prevent the drainage stent 450 from migrating once it has been deployed between the pseudocyst and the gastrointestinal tract. The retention features 458a, 458b may be positioned on an outer surface of the stent 450. The stent 450 may be formed having the final expanded shape and heated and deformed to be loaded onto a delivery balloon. It is contemplated that the delivery balloon may be generally straight. During deployment of the stent 450, application of heat may cause the stent 450 to return to its remembered or expanded shape.

Figure 9:
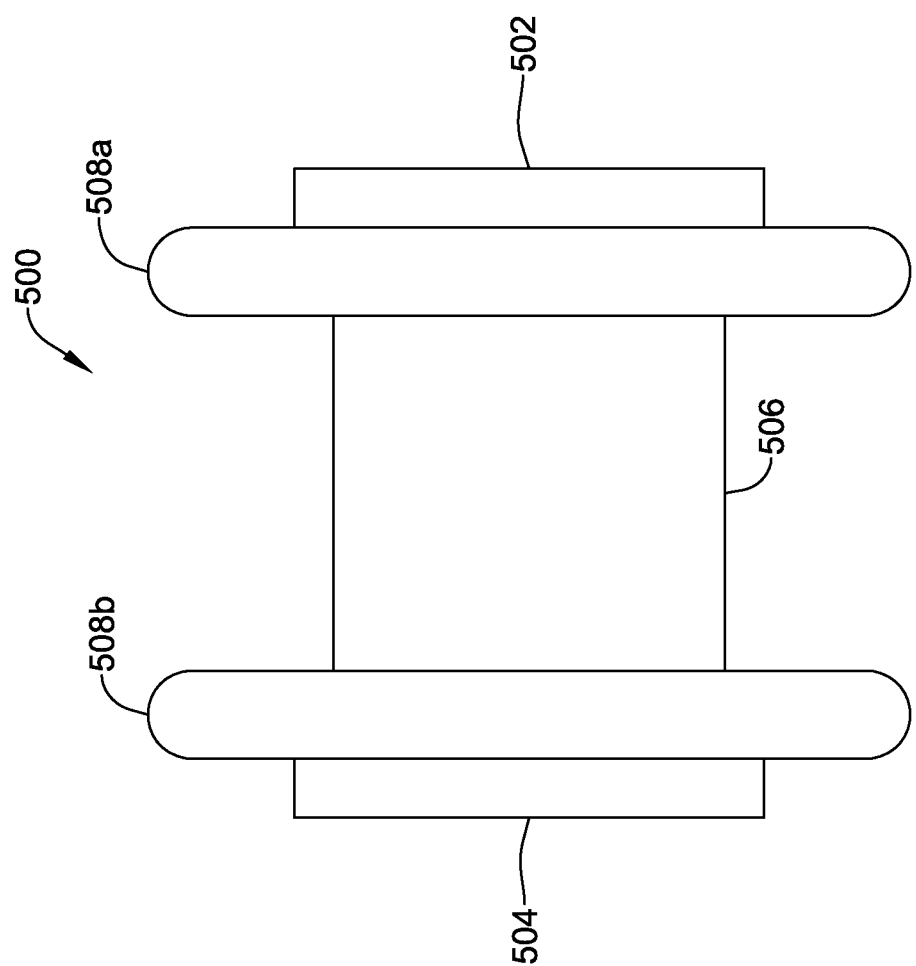
FIG. 9 is a perspective view of another illustrative stent.

FIG. 9 illustrates another illustrative self expanding stent 500. The stent 500 may be formed from a shape memory polymer. The stent 500 may be molded in its expanded configuration, with a large diameter and anti-migration features. The stent 500 may be cross-linked in this state, meaning that the expanded configuration is the remembered shape of the stent 500. The stent 500 may include a proximal end 502 and a distal end 504. The stent 500 may have a generally tubular intermediate region 506 extending between the proximal end 502 and the distal end 504. The inner diameter of the stent 500 adjacent to the proximal and distal ends 502, 504 may be larger than the inner diameter of the stent in the intermediate region 506, although this is not required. The stent 500 may further include a pair of retention features 508a, 508b positioned adjacent to the proximal and distal ends 502, 504. The retention features 508a, 508b may be generally ring shaped protrusions extending from an outer surface of the stent 500. In some instances, the retention features 508a, 508b may have an outer diameter that is larger than the outer diameter at any of the proximal end 502, distal end 504, or intermediate region 506. The retention features 508a, 508b may be sized and shaped to prevent the drainage stent 500 from migrating once it has been deployed between the pseudocyst and the gastrointestinal tract. The stent 500 may be formed having the final expanded shape and heated and deformed to be loaded onto a delivery balloon. It is contemplated that the delivery balloon may be generally straight. During deployment of the stent 500, application of heat may cause the stent 500 to return to its remembered or expanded shape.

Figure 10:
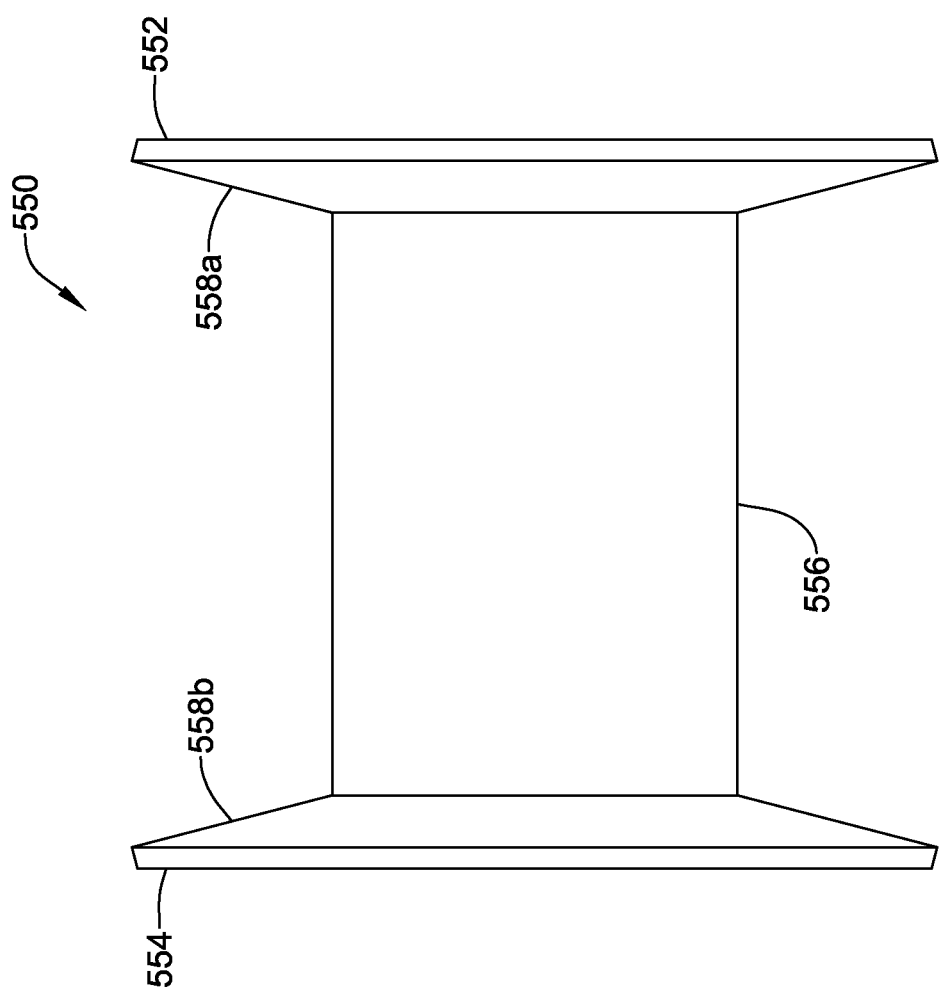
FIG. 10 is a perspective view of another illustrative stent.

FIG. 10 illustrates another illustrative self expanding stent 550. The stent 550 may be formed from a shape memory polymer. The stent 550 may be molded in its expanded configuration, with a large diameter and anti-migration features. The stent 550 may be cross-linked in this state, meaning that the expanded configuration is the remembered shape of the stent 550. The stent 550 may include a proximal end 552 and a distal end 554. The stent 550 may have a generally tubular intermediate region 556 positions between the proximal end 552 and the distal end 554. The inner diameter of the stent 550 may be generally constant or uniform in the intermediate region 556. The stent 550 may further include a pair of retention features 558a, 558b positioned adjacent to the proximal and distal ends 552, 554. The retention features 558a, 558b may be outwardly facing flares. For example, the proximal retention feature 558a may increase in diameter from the intermediate region 556 towards the proximal end 552. The distal retention feature 558b may increase in diameter from the intermediate region 556 towards the distal end 455. In some instances, the taper 560a. 560b of the retention features 558a, 558b may be steep such that retention features 558a, 558b do not cause further dilation of the opening in the pseudocyst and/or gastrointestinal tract wall. The retention features 558a, 558b may be sized and shaped to prevent the drainage stent 550 from migrating once it has been deployed between the pseudocyst and the gastrointestinal tract. The stent 550 may be formed having the final expanded shape and heated and deformed to be loaded onto a delivery balloon. It is contemplated that the delivery balloon may be generally straight. During deployment of the stent 550, application of heat may cause the stent 550 to return to its remembered or expanded shape. It is further contemplated that stent 550 may be formed in a generally tubular, unexpanded configuration. In this instance, stent 550 may be molded into the expanded configuration during deployment utilizing heat and a shaped delivery balloon having an outer surface profile corresponding to the desired final shape of the stent 550.

The materials that can be used for the various components of systems 10, 200, 300, 350, 400, 450, 500, 550 (and/or other systems disclosed herein) may include those commonly associated with medical devices. For simplicity purposes, the following discussion makes reference to catheter shaft 12. However, this is not intended to limit the systems and methods described herein, as the discussion may be applied to other components in systems 10, 200, 300, 350, 400, 450, 500, 550.

Catheter shaft 12 and/or other components of systems 10, 200, 300, 350, 400, 450, 500, 550 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about-60 degrees Celsius (C) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In other embodiments, a superelastic alloy, for example a superelastic nitinol can be used to achieve desired properties.

In at least some embodiments, portions or all of system 10, 200, 300, 350, 400, 450, 500, 550 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of systems 10, 200, 300, 350, 400, 450, 500, 550 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10, 200, 300, 350, 400, 450, 500, 550 to achieve the same result.

In some embodiments, a degree of Magnetic Resonance Imaging (MRI) compatibility is imparted into systems 10, 200, 300, 350, 400, 450, 500, 550. For example, catheter shaft 12 or portions thereof, may be made of a material that does not substantially distort the image and create substantial artifacts (i.e., gaps in the image). Certain ferromagnetic materials, for example, may not be suitable because they may create artifacts in an MRI image. Catheter shaft 12 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be suitable for use in systems 10, 200, 300, 350, 400, 450, 500, 550 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope of the present disclosure as described in the appended claims.

What is claimed is:

1. A stent delivery catheter, comprising:
   a catheter shaft having a proximal end and a distal end;
   wherein the catheter shaft further comprises an inner member and an outer member;
   an inflatable balloon having an inner region and an outer surface, the inflatable balloon disposed adjacent to the distal end of the catheter shaft;
   a cutting electrode disposed on the distal end of the inner member of the catheter shaft; and
   a self-expanding stent disposed about the catheter shaft and adjacent to the distal end, the stent having a non-expanded state and an expanded state, wherein the stent in the expanded state comprises a proximal retention feature and a distal retention feature,
   wherein the distal retention feature increases in diameter from a distal end of the self-expanding stent towards a proximal end of the self-expanding stent,
   wherein the proximal retention feature increases in diameter from the proximal end of the self-expanding stent towards the distal end of the self-expanding stent, and
   wherein at least one of the proximal or distal retention features are configured to engage an interior portion of a pseudocyst or a gastric structure to prevent migration of the self-expanding stent.

2. The stent delivery catheter of claim 1, wherein the expanded state of the stent includes a flared proximal end region and a flared distal end region.

3. The stent delivery catheter of claim 2, wherein the flared proximal end region and the flared distal end region each comprise an inwardly facing flare portion.

4. The stent delivery catheter of claim 1, wherein an outer diameter of the inflatable balloon varies along the inflatable balloon.

5. The stent delivery catheter of claim 4, wherein the inflatable balloon has a first region having a first outer diameter, a second region having a second outer diameter, and
   a third region having a third outer diameter, the second diameter smaller than the first and third diameters, and wherein the stent in the expanded state comprises a shape substantially corresponding to the first region, the second region, and the third region of the inflatable balloon.

6. The stent delivery catheter of claim 5, wherein the stent is disposed in the non-expanded state about the outer surface of the inflatable balloon along the first region, the second region, and the third region.

7. The stent delivery catheter of claim 1, wherein the stent is configured to create a drainage path between a gastrointestinal tract lumen and a pseudocyst.

8. A method for delivering a stent between a first body lumen and a second body lumen, the method comprising:
   advancing a stent delivery catheter to a target location within the first body lumen, the catheter comprising:
   a catheter shaft extending from a proximal end to a distal end;
   wherein the catheter shaft further comprises an inner member and an outer member;
   an inflatable balloon disposed along the catheter shaft proximate the distal end of the catheter shaft;
   a cutting electrode positioned at the distal end of the inner member of the catheter shaft; and
   a stent disposed about the catheter shaft proximate the distal end of the catheter shaft, the stent having a first unexpanded configuration and a second expanded configuration;
   energizing the cutting electrode in contact with the first body lumen to create an opening from the first body lumen;
   energizing the cutting electrode in contact with the second body lumen to create an opening to the second body lumen;
   inflating the inflatable balloon within the opening from the first body lumen and the opening to the second body lumen; and
   deploying the stent to the second expanded configuration within the opening from the first body lumen and the opening to the second body lumen,
   wherein the stent in the expanded configuration comprises a proximal retention feature and a distal retention feature,
   wherein the distal retention feature increases in diameter from a distal end of the self-expanding stent towards a proximal end of the self-expanding stent,
   wherein the proximal retention feature increases in diameter from the proximal end of the self-expanding stent towards the distal end of the self-expanding stent, and
   wherein at least one of the proximal or distal retention features are configured to engage an interior portion of a pseudocyst or a gastric structure to prevent migration of the self-expanding stent.

9. The method of claim 8, wherein in the second expanded configuration, the stent comprises a proximal retention member, a distal retention member, or both.

10. The method of claim 9, wherein the proximal retention member, the distal retention member, or each of the proximal retention member and the distal retention member comprises a flared end region.

11. The method of claim 9, wherein deploying the stent results in the proximal retention member being positioned within the first body lumen, the distal retention member being positioned within the second body lumen, or both.

12. The method of claim 8, wherein an outer diameter of the inflatable balloon varies along the inflatable balloon.

13. The method of claim 12, wherein the stent in the second expanded configuration substantially corresponds to the varying outer diameter of the inflatable balloon.

14. The method of claim 8, wherein the stent comprises a bioabsorbable shape memory polymer configured to expand when exposed to body temperature.

15. A method for delivering a stent between a first body lumen and a second body lumen, the method comprising:
   advancing a stent delivery catheter to a target location within the first body lumen, the catheter comprising:

a catheter shaft having a proximal end and a distal end;
wherein the catheter shaft further comprises an inner member and an outer member;
an inflatable balloon disposed along the catheter shaft adjacent to the distal end of the catheter shaft;
a cutting electrode disposed on the distal end of the inner member of the catheter shaft; and
a stent disposed about the catheter shaft, the stent having a non-expanded state and an expanded state;
energizing the cutting electrode in contact with the first body lumen to create an opening from the first body lumen;
energizing the cutting electrode in contact with the second body lumen, through the opening from the first body lumen, to create an opening to access the second body lumen;
inflating the inflatable balloon within one or both of the opening from the first body lumen and the opening to the second body lumen; and
transforming the stent to the expanded state across the opening from the first body lumen and through the opening to the second body lumen,
wherein the stent in the expanded state comprises a proximal retention feature and a distal retention feature,
wherein the distal retention feature increases in diameter from a distal end of the self-expanding stent towards a proximal end of the self-expanding stent,
wherein the proximal retention feature increases in diameter from the proximal end of the self-expanding stent towards the distal end of the self-expanding stent, and
wherein at least one of the proximal or distal retention features are configured to engage an interior portion of a pseudocyst or a gastric structure to prevent migration of the self-expanding stent.

16. The method of claim 15, wherein in the expanded state, the stent comprises a proximal retention member, a distal retention member, or both.

17. The method of claim 16, wherein the proximal retention member, the distal retention member, or each of the proximal retention member and the distal retention member comprises a flared end region.

18. The method of claim 16, wherein transforming the stent to the expanded state across the openings includes positioning the proximal retention member within the first body lumen, positioning the distal retention member within the second body lumen, or both.

19. The method of claim 15, wherein an outer diameter of the inflatable balloon varies along the proximal end to the distal end of the inflatable balloon.

20. The method of claim 15, wherein the first body lumen is a gastrointestinal tract lumen and the second body lumen is a pseudocyst.

\* \* \* \* \*